United States Patent [19]

Welch et al.

[11] Patent Number: 5,534,473
[45] Date of Patent: Jul. 9, 1996

[54] CATALYST SYSTEMS FOR PRODUCING BROAD MOLECULAR WEIGHT POLYOLEFIN

[75] Inventors: M. Bruce Welch; Rolf L. Geerts; Syriac J. Palackal, all of Bartlesville, Okla.; Ted M. Pettijohn, Marshall, Tex.

[73] Assignee: Phillips Petroleum Company, Bartlesville, Okla.

[21] Appl. No.: 463,839

[22] Filed: Jun. 5, 1995

Related U.S. Application Data

[60] Division of Ser. No. 305,243, Sep. 13, 1994, which is a continuation-in-part of Ser. No. 226,600, Apr. 12, 1994, abandoned, which is a continuation-in-part of Ser. No. 192,223, Feb. 3, 1994, which is a continuation-in-part of Ser. No. 734,853, Jul. 23, 1991, Pat. No. 5,436,305.

[51] Int. Cl.$^6$ .................................................. C08F 4/643
[52] U.S. Cl. ..................... 502/117; 502/103; 502/113; 502/152; 526/118; 526/119; 526/132; 526/134; 526/160
[58] Field of Search .................................. 526/118, 119, 526/160, 132, 134; 502/113, 117, 152, 103

[56] References Cited

U.S. PATENT DOCUMENTS 4,935,474  6/1990  Ewen et al. ...................... 526/119 X
4,939,217  7/1990  Stricklen ........................... 526/119 X Primary Examiner—Fred Teskin
Attorney, Agent, or Firm—Edward L. Bowman

[57] ABSTRACT

A catalyst system comprising a bridged fluorenyl-containing metallocene, an unbridged metallocene, and a suitable cocatalyst and the use of such catalyst systems to produce olefin polymers. Also novel olefin polymers produced by those processes.

8 Claims, No Drawings

CATALYST SYSTEMS FOR PRODUCING BROAD MOLECULAR WEIGHT POLYOLEFIN

This application is a division of application Ser. No. 08/305,243, filed Sep. 13, 1994, now pending, which is a continuation-in-part of U.S. patent application Ser. No. 08/226,600 filed Apr. 12, 1994, now abandoned which was a continuation-in-part of U.S. patent application Ser. No. 08/192,223 filed Feb. 3, 1994, which was a continuation-in-part of U.S. patent application Ser. No. 07/734,853 filed Jul. 23, 1991, now U.S. Pat. No. 5,436,305. The disclosure of all those applications are incorporated herein by reference.

FIELD OF THE INVENTION

The present invention relates to the polymerization of olefins. More specifically, the present invention relates to the polymerization of olefins using metallocene catalyst systems. Still more specifically, the present invention relates to metallocene catalyst systems and processes suitable for producing useful polyolefins having broadened molecular weight distributions.

BACKGROUND OF THE INVENTION

One of the unique features of many metallocene catalysts is that they tend to produce polyolefins having a narrow molecular weight distribution. While the narrow molecular weight distribution has benefits in some applications, for other applications there is often a need for a polyolefin product having a broader molecular weight distribution. For example, while narrow molecular weight distribution polymers are often suitable for injection molding, and possibly for the production of fibers, other applications such as thermoforming, extrusion, blow molding, and the production of foams or film often are found to perform better with polymers having a broader molecular weight distribution.

In the past there have been some patents which suggest the employment of a mixture of metallocenes to produce polymers having broadened molecular weight distributions. Examples of those patents include U.S. Pat. No. 4,530,914 and 4,937,299. While these two patents at least suggest that a wide range of mixtures of metallocenes could be employed in producing the broadened molecular weight distribution, all examples in those patents involve the employment of unbridged metallocenes. The applicants' recent research has revealed that many unbridged metallocenes are particularly sensitive to the presence of hydrogen. Accordingly, some combinations of unbridged metallocenes while producing a broadened molecular distribution when used in the presence of hydrogen produce polymers having such low molecular weight that they would not be suitable for many applications.

An object of the present invention is to provide a mixed metallocene catalyst system which is capable of giving broad molecular weight distributions over a wide range of polymerization conditions, including polymerizations employing a wide range of hydrogen levels. Particularly preferred embodiments produce polymer products having a molecular weight distribution greater than 8, even more preferably greater than 30.

In accordance with another aspect of the present invention, there are provided catalyst systems capable of producing unusual copolymers in which the comonomer incorporation is incorporated mainly in the high molecular weight end of the molecular weight distribution.

In accordance with yet another aspect of the present invention, there are provided catalyst systems capable of providing ethylene copolymers of broad molecular weight distribution which have high environmental stress crack resistance.

SUMMARY OF THE INVENTION

In accordance with the present invention, there is provided a catalyst system suitable for preparing a polyolefin having a broad molecular weight distribution, i.e. a $M_w/M_n$ of greater than 3, from an olefin or mixture of olefins. The inventive catalyst system comprises (1) at least first and second different metallocenes characterized by the fact that the first metallocene is a bridged metallocene which contains a fluorenyl group, and said second metallocene is an unbridged metallocene and by the fact that the first metallocene if used as the sole metallocene produces a higher molecular weight than said second metallocene would produce if used as the sole metallocene under the same polymerization conditions, and (2) a suitable cocatalyst for the metallocenes.

Also in accordance with the present invention, there is provided the method for producing a polyolefin comprising contacting at least one olefin under suitable polymerization conditions with the inventive catalyst system.

Still another aspect of the present invention is the polymers produced by polymerizing an olefin using the inventive catalyst system.

DETAILED DESCRIPTION OF THE INVENTION

The term "bridged metallocene" as used herein refers to a metallocene in which two cyclopentadienyl-type groups are connected by bridging structure. Cyclopentadienyl-type groups refer to organic groups containing cyclopentadienyl structure such as cyclopentadienyl, fluorenyl, indenyl, tetrahydroindenyl, benzofluorenyl, octahydrofluorenyl, and substituted variations thereof. The bridged metallocenes employed in the present invention are fluorenyl-containing metallocenes. Unless specifically noted elsewhere, the bonding of the fluorenyl to the bridge is through the 9 position on the fluorenyl. Such fluorenyl-containing metallocenes include compounds of the formula $(Z)-R'-(Z')MeQ_k$ wherein R' is an organo group linking Z and Z', Z is a substituted or unsubstituted fluorenyl radical, Z' is a substituted or unsubstituted fluorenyl radical, a substituted or unsubstituted indenyl radical, a substituted or unsubstituted cyclopentadienyl radical, a tetrahydroindenyl radical, or an octahydrofluorenyl radical. The substituents on Z and Z' can be selected from generally any substituents which do not preclude the metallocene from having the desired activity. Me is a transition metal selected from the elements of Groups IVB, VB, or VIB of the Periodic Table. Each Q can be the same or different and can be selected from a monovalent group consisting of hydrogen, halogen, a hydrocarbyl group having 1 to 20 carbon atoms, an alkoxy group having 1 to 20 atoms, an amino group which may or may not be substituted with up to two hydrocarbyl groups having 1 to 20 carbons, a phosphorus-containing hydrocarbyl group having 1 to 20 carbon atoms, and a silicon-containing hydrocarbyl group having 1 to 20 carbons, and an aluminum-containing hydrocarbyl group having 1 to 20 carbon atoms. In the more preferred embodiments both Z and Z' are bound to Me. This is often referred to as sandwich bonding.

Some examples of bridging groups include hydrocarbyl alkylene radicals, divalent dihydrocarbyl germanium radicals, divalent dihydrocarbyl silyl radicals, divalent hydrocarbyl phosphine radicals, divalent hydrocarbyl amine radicals, and divalent dihydrocarbyl tin radicals. Still more examples are provided in U.S. Pat. No. 5,087,677 column 5, lines 10–45. Still others are disclosed in U.S. Pat. No. 4,975,403 column 4, lines 15–26 and U.S. Pat. No. 5,132,381 column 2, lines 41–65.

A number of examples of such bridged fluorenyl-containing metallocenes and methods for preparing them are disclosed in published European Application No. 524,624. Some specific examples of sandwich bonded bridged fluorenyl-containing metallocenes in which Me is zirconium and each Q is chloride include:

1) 1-(fluorenyl)-1-(cyclopentadienyl) methane zirconium dichloride, 2) 1-(fluorenyl)-1-(indenyl) methane zirconium dichloride, 3) 1-(2,7-di-t-butylfluorenyl)-1,1-(dimethyl)-1-(cyclopentadienyl) methane zirconium dichloride, 4) 1-(2,7-di-bromofluorenyl)-1,1-(dimethyl)-1-(cyclopentadienyl) methane zirconium dichloride, 5) 1-(2,7-di-methylfluorenyl)-1,1-(dimethyl)-1-(cyclopentadienyl) methane zirconium dichloride, 6) 1-(2,7-di-phenylfluorenyl)-1,1-(dimethyl)-1-(cyclopentadienyl) methane zirconium dichloride, 7) 1-(2,7-diphenylfluorenyl)-1,1-(diphenyl)-1-(cyclopentadienyl) methane zirconium dichloride, 8) 5-(fluorenyl)-5-(cyclopentadienyl)-1-hexene zirconium dichloride, 9) 1-(2,7-di-t-butylfluorenyl)-1,1-(diphenyl)-1-(cyclopentadienyl) methane zirconium dichloride, 10) 1-(fluorenyl)-1-(cyclopentadienyl)-1-(n-butyl)-1-(methyl) methane zirconium dichloride, 11) 1-(2,7-dichlorofluorenyl)-1,1-(diphenyl)-1-(cyclopentadienyl) methane zirconium dichloride, 12) 1-(fluorenyl)-1-(cyclopentadienyl) cyclopentane zirconium dichloride, 13) 1-(fluorenyl)-1-(cyclopentadienyl)-1-(3-cyclohexenyl) methane zirconium dichloride, 14) 1-(fluorenyl)-1-(2-allylcyclopentadienyl)-1,1-(dimethyl) methane zirconium dichloride, 15) 1-(2,7-di-methylvinylfluorenyl)-1-(cyclopentadienyl)-1,1-(dimethyl) methane zirconium dichloride, 16) 1-(fluorenyl)-1-(2-trimethylsilylcyclopentadienyl)-1,1-(dimethyl) methane zirconium dichloride, 17) 1-(fluorenyl)-1-(cyclopentadienyl)-1-(para-methoxyphenyl) methane zirconium dichloride, 18) bis(1-methylfluorenyl) methane zirconium dichloride, 19) 1-(fluorenyl)-1-(cyclopentadienyl)-1-(phenyl)methane zirconium dichloride, 20) 7-(fluorenyl)-2-(cyclopentadienyl)-(adamantyl) zirconium dichloride, 21) 1-(2,7-di-mesitylfluorenyl)-1-(cyclopentadienyl)-1,1-(dimethyl) methane zirconium dichloride, 22) 1-(2-phenylfluorenyl)-1,1-(dimethyl)-1-(cyclopentadienyl) methane zirconium dichloride, 23) 1-(2,7-dimethoxyfluorenyl)-1,1-(diphenyl)-1-(cyclopentadienyl) methane zirconium dichloride, 24) 1-(2,7-dimesitylfluorenyl)-1-(cyclopentadienyl) cyclopentane zirconium dichloride, 25) 1-(2,7-diphenylfluorenyl)-1-(cyclopentadienyl)-1-(phenyl) methane zirconium dichloride, 26) 1-(3,4-dimethylfluorenyl)-1-(cyclopentadienyl)-1-(phenyl) methane zirconium dichloride, 27) 1-(fluorenyl)-2-(indenyl) ethane zirconium dichloride, also known as 1-(fluorenyl)-2-(indenyl) ethylene zirconium dichloride, 28) 1-(4-methylfluorenyl)-2-(1-methylfluorenyl) ethane zirconium dichloride, 29) 1-(fluorenyl)-2-(cyclopentadienyl) ethane zirconium dichloride, 30) 1-(fluorenyl)-3-(cyclopentadienyl) propane zirconium dichloride, 31) 1-(fluorenyl)-1-(cyclopentadienyl)-1,1-(diphenyl) germanyl zirconium dichloride, 32) 1-(fluorenyl)-1-(cyclopentadienyl)-1,1-(dimethyl) silylene zirconium dichloride, 33) 1,1-bis(fluorenyl)-1,1-(dimethyl) silylene zirconium dichloride, also sometimes referred to as bis(fluorenyl)-dimethyl silyl zirconium dichloride or bis(fluorenyl) (dimethyl) silane zirconium dichloride.

34) 1-(fluorenyl)-1-(cyclopentadienyl)-1-(methyl) aluminum zirconium dichloride, 35) bis(1-methylfluorenyl)-(dimethyl) tin zirconium dichloride, 36) bis(1-methylfluorenyl)-(diphenyl) tin zirconium dichloride, 37) bis(1-methylfluorenyl)-(dimethyl) silylene zirconium dichloride, 38) 1,2-di(3,4-benzofluorenyl) ethane zirconium dichloride, and 39) 1-(3,4-benzofluorenyl)-1-(cyclopentadienyl)-1,1-(dimethyl) methane zirconium dichloride.

Other examples of bridged fluorenyl-containing metallocenes include those disclosed in published European Application No. 574,258, the disclosure of which is incorporated herein by reference. Still other bridged fluorenyl-containing metallocenes include the fluorenyl-containing metallocenes of formula Ia of published Canadian Patent Application No. 2,069,602, and those disclosed in U.S. Pat. No. 5,281,679, the disclosures of which are incorporated herein by reference. Still other examples include compounds similar to those of the formulas disclosed in U.S. Pat. No. 5,324,800, column 4, lines 23–25, wherein the metallocenes differ in that at least one $(C_5R'_m)$ is a fluorenyl-containing radical. The term "bridged metallocene" also includes metallocene-containing polymers produced from a bridged fluorenyl-containing metallocene having polymerizable unsaturation using a procedure of the type disclosed in EPC published application No. 586,167, the disclosure of which is incorporated herein by reference. One particularly preferred metallocene-containing polymer is the polymer produced by prepolymerizing 5-(fluorenyl)-5-(cyclopentadienyl)-1-hexene zirconium dichloride with ethylene. It is also within the scope of the invention to use a catalyst system comprising a metallocene-containing polymer produced by copolymerizing a bridged fluorenyl-containing metallocene having polymerizable unsaturation with an unbridged metallocene having polymerizable unsaturation in the presence or absence of further comonomers such as ethylene.

The term "unbridged metallocene" as used herein refers to those metallocenes which do not have two cyclopentadienyl-type radicals connected to each other by a bridging structure. The association of two cyclopentadienyl radicals by the transition metal of the metallocene is not viewed herein as a bridging structure. Various techniques have been developed for producing such metallocenes. Examples are disclosed in the aforementioned U.S. Pat. No. 5,324,800, U.S. Pat. No. 5,281,679, and in EPC Application No. 524,624, the disclosures of which are incorporated herein by reference.

Some specific examples of what is meant by unbridged zirconium halide metallocenes include 1) (fluorenyl)(cyclopentadienyl) zirconium dichloride, 2) bis(n-butyl cyclopentadienyl) zirconium dichloride, 3) (9-methylfluorenyl)(cyclopentadienyl) zirconium dichloride, 4) (1-prop-2-enyl indenyl)(cyclopentadienyl) zirconium dichloride, 5) (indenyl)(pentamethylcyclopentadienyl) zirconium dichloride, 6) (fluorenyl)(cyclopentadienyl) zirconium dichloride, 7) (fluorenyl)(pentamethylcyclopentadenyl) zirconium dichloride, 8) bis(t-butylcyclopentadienyl) zirconium dichloride, 9) bis(iso-pentylcyclopentadienyl) zirconium dichloride, 10) bis(isopropylcyclopentadienyl) zirconium dichloride, 11) bis(3,4-benzofluorenyl) zirconium dichloride, 12) (3,4-benzofluorenyl)(cyclopentadienyl) zirconium dichloride, 13) (2,3:6,7-dibenzofluorenyl)(cyclopentadienyl) zirconium dichloride, 14) (2,7-dimethylfluorenyl)(pentamethylcyclopentadienyl) zirconium dichloride, 15) (2,7-di-t-butylfluorenyl)(pentamethylcyclopentadienyl) zirconium dichloride, 16) bis(1-methylfluorenyl) zirconium dichloride, 17) bis(methylcyclopentadienyl)(2,7-dimethylfluorenyl) zirconium chloride, 18) (9-phenylfluorenyl)(cyclopentadienyl) zirconium dichloride, 19) (9-cyclohexylfluorenyl)(cyclopemadienyl) zirconium dichloride, 20) (9-isopropylfluorenyl)(cyclopentadienyl) zirconium dichloride, 21) bis(9-prop-2-enyl fluorenyl) zirconium dichloride, 22) (9-(3-cyclopent-1-enyl) fluorenyl)(cyclopentadienyl) zirconium dichloride, 23) bis(1-but-3-enylindenyl) zirconium dichloride, 24) bis(9-hex-5-enylfluorenyl) zirconium dichloride, and 25) (9-tert-butylfluorenyl)(cyclopentadienyl) zirconium dichloride.

Some currently preferred particular combinations of bridged and unbridged metallocenes include 1) (9-methylfluorenyl)(cyclopentadienyl) zirconium dichloride plus bis(9-fluorenyl) dimethyl silyl zirconium dichloride, 2) bis(n-butylcyclopentadienyl) zirconium dichloride plus 1,2-bis(9-fluorenyl) ethane zirconium dichloride, 3) bis(n-butylcyclopentadienyl) zirconium dichloride plus bis(9-fluorenyl) dimethyl silyl zirconium dichloride, 4) (cyclopentadienyl)(fluorenyl) zirconium dichloride plus bis(9-fluorenyl) dimethyl silyl zirconium dichloride, 5) (cyclopentadienyl)(fluorenyl) zirconium dichloride plus 1-(cyclopentadienyl)-1-(9-fluorenyl) methane zirconium dichloride, 6) (cyclopentadienyl)(fluorenyl) zirconium dichloride plus 1-(indenyl)-2-(9-fluorenyl) ethane zirconium dichloride, 7) (9-methylfluorenyl)(cyclopentadienyl) zirconium dichloride plus 1-(cyclopentadienyl)-1-(9-fluorenyl) methane zirconium dichloride, 8) (9-methylfluorenyl)(cyclopentadienyl) zirconium dichloride plus 1-(2,7-diphenylfluorenyl)-1-(cyclopentadienyl)-1,1-diphenylmethane zirconium dichloride, 9) (cyclopentadienyl)(fluorenyl) zirconium dichloride plus 1-(2,7-diphenylfluorenyl)-1-(cyclopentadienyl)-1,1-(diphenyl)(methane) zirconium dichloride, 10) (9-methylfluorenyl)(cyclopentadienyl) zirconium dichloride plus bis(9-fluorenyl)(diphenyl) silyl zirconium dichloride, 11) bis(n-butylcyclopentadienyl) zirconium dichloride plus 1-(indenyl)-2-(9-fluorenyl) ethane zirconium dichloride, and 12) (cyclopentadienyl)(fluorenyl) zirconium dichloride plus 1-(indenyl)-2-(9-fluorenyl) ethane zirconium dichloride.

The molar ratio of the unbridged metallocene to the bridged metallocene can vary over a wide range depending upon the particular results desired and the particular polymerization conditions under which they will be employed. Typically, the molar ratio of the bridged fluorenyl-containing metallocene to the unbridged metallocene will be in the range of from about 10000/1 to about 1/1000 or more typically 99/1 to 1/99. Typically the molar ratio of the bridged and unbridged metallocenes is determiend by considering the relative activities of the catalysts and determining the extent of contribution desired to be provided by each metallocene. In a particularly preferred embodiment, bridged and unbridged metallocenes are selected which produce a broader molecular weight distribution than either would produce under the same polymerization conditions if employed in the absence of the other metallocene. Still further, in another preferred embodiment, bridged and unbridged metallocenes are selected which have the capability of producing significantly different weight average molecular weights so that when the two are used together, there will be a clear bimodal molecular weight distribution.

The resulting combination of the bridged fluorenyl-containing metallocene and the unbridged metallocene can be used in combination with a suitable cocatalyst of the polymerization of olefinic monomers.

Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion techniques such as disclosed in U.S. Pat. No. 5,155,080, e.g. using triphenyl carbenium tetrakis (pentafluorophenyl) boronate. Another example would be the use a mixture of trimethylaluminum and dimethylfluoroaluminum such as disclosed by Zambelli et, *Macromolecules*, 22, 2186 (1989). In such processes the metallocene or the cocatalyst can be employed on a solid insoluble support.

The currently most preferred cocatalyst is an aluminoxane. Such compounds include those compounds having repeating units of the formula

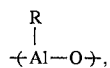

where R is an alkyl group generally having 1 to 5 carbon atoms.

Aluminoxanes, also sometimes referred to as poly(hydrocarbyl aluminum oxides) are well known in the art and are generally prepared by reacting an hydrocarbylaluminum compound with water. Such a preparation techniques are disclosed in U.S. Pat. Nos. 3,242,099 and 4,808,561, the disclosures of which are incorporated herein by reference. The currently preferred aluminoxane cocatalysts are prepared either from trimethylaluminum or triethylaluminum and are sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In some cases polymerizations would be carried out in a homogeneous system in which the catalyst and cocatalyst were soluble; however, it is within the scope of the present invention to carry out the polymerizations in the presence of solid forms of the catalyst and/or cocatalyst in a slurry, gas, or solution phase polymerization.

Generally the molar ratio of the aluminum in the organoaluminoxy cocatalyst to the transition metal in the metallocenes would be in the range of about 1:1 to about 100,000:1 and more preferably about 5:1 to about 15,000:1. As a general role, the polymerizations would be carried out in the presence of liquid diluents which do not have an adverse affect upon the catalyst system. Examples of such liquid diluents include propane, butane, isobutane, pentane, hexane, heptane, octane, cyclohexane, methylcyclohexane, toluene, xylene, and the like. The polymerization temperature can vary over a wide range, temperatures typically would be in the range of about −60° C. to about 300° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer.

In a particular preferred embodiment, the mixture of metallocenes is employed in combination with a solid organoaluminoxane which is substantially insoluble in polymerization diluents under particle form polymerization conditions. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640.

Still another technique involves contacting an organoaluminoxane with an organic borane compound free of acidic hydrogen as taught in pending U.S. patent application Ser. No. 08/080,899 filed Jun. 22, 1993, now U.S. Pat. No. 5,354,721, the disclosure of which is incorporated herein by reference. Yet another technique involves contacting an organoaluminoxane with an organoboron comopund having boron acid functionality, i.e. —BOH, as taught in pending U.S. patent application Ser. No. 08/092,143 filed Jul. 14, 1993, now U.S. Pat. No. 5,414,180 the disclosure of which is incororated herein by reference. The currently preferred technique for preparing the solid organoaluminoxy cocatalyst involves contacting an organic solution of an organoaluminoxane optionally containing trialkylaluminums with a suitable organoboroxine compound as taught in copending U.S. patent application No. 08/017,207 filed Feb. 12, 1993, now U.S. Pat. No. 5,411,925 the disclosure of which is incorporated herein by reference.

Various boroxines are known in the art. The term organo boroxine as used herein refers to compounds of the formula (RBO) wherein each R is the same or a different organo group free of hydroxyl (HO—) or mercapto (HS—) groups. The R groups could include such radicals as methyl, ethyl, isopropyl, tertiary butyl, 2-ethyl ethylene, tri-n-butyl methyl, o-tolyl, phenyl, o-tri-fluoro methyl phenyl, o-chloro-phenyl, 2,6-dimethyl phenyl, $C_2H_5$—S—$CH_2CH_2CH_2$—, $CH_2$=CH—$CH_2$—, α-naphthyl, β-naphthyl, and the like. The R groups could also be R'O—, R'S—, $R_2'N$—, $R_2'P$—, and $R_3'Si$— wherein each R' is a hydrocarbyl group. Generally each R group contains about 1 to about 25 carbon atoms, more typically 1 to 10 carbon atoms. Especially preferred are the hydrocarbyl boroxines and the hydrocarbyl oxy boroxines. Examples of hydrocarbyl boroxines include trimethyl boroxine, triethyl boroxine, tri-n-propyl boroxine, tributyl boroxine, tricyclohexyl boroxine, triphenyl boroxine, methyl diethyl boroxine, dimethylethyl boroxine, and the like. The currently preferred hydrocarbyl boroxines are trimethyl boroxine and triethyl boroxine. The term hydrocarbyloxy boroxine refers to compounds of the formula ((R'O)BO) wherein each R' can be the same or different hydrocarbyl group, generally containing about 1 to about 10 carbon atoms. Trialkyloxy boroxines are currently preferred. Trimethoxy boroxine is an example.

The reaction of the boroxine with the aluminoxane can be carried out in any suitable manner. One particularly desirable technique simply involves contacting the two reactants in a suitable liquid diluent. One preferred technique involves contacting a hydrocarbon solution of the aluminoxane with a hydrocarbon solution of the boroxine. Another technique involves contacting a hydrocarbon solution of the aluminoxane with a countersolvent to produce a slurry comprising soluble aluminoxane and insoluble particulate aluminoxane and then contacting the resulting slurry with a solution of the boroxine. It is also within the scope of the present invention to carry out the reaction of the boroxine and the aluminoxane in the presence of a particulate diluent so that the insoluble product becomes deposited upon the particulate diluent. Typical particulate diluents would include such inorganic materials as silica, alumina, aluminum phosphate, silica-alumina, titania, kaolin, fumed silica, and the like.

It is also within the scope of the present invention to prepare the inventive particulate organo-aluminoxy composition and then combine it with a solution of a trialkylaluminum compound, e.g. trimethylaluminum or others of the type mentioned above, and then to contact the resulting slurry with additional boroxine of the type described above. It is believed that this process may provide a method for further increasing the molecular weight of the particulate aluminoxy composition that is initially produced by reacting the aluminoxane with the boroxine. Obviously, such a process could be repeated several times to obtain the desired level of molecular weight, particle size, bulk density, or other characteristic that is desired for a particular application.

The amount of boroxine employed relative to the aluminoxane can vary over a wide range depending upon the particular results desired. A technique which has been used in this invention for reflecting the ratio of boroxine to aluminoxane, involves the use of a calculated amount for the amount of aluminoxy aluminum in the aluminoxane solution. As used herein the term calculated aluminum is the value obtained by using a vacuum to strip the solvent off a known volume of the aluminoxane solution; weighing the recovered solid; and dividing the weight of the solid per milliter by the average molecular weight of the aluminoxy units,

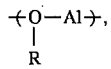

i.e. 58 for methylaluminoxane, so that one obtains a calculated value for the number of moles of aluminum per volume of the aluminoxane solution that is to be reacted with the boroxine. It is theorized that a substantial portion of any free trihydrocarbyl aluminum in the aluminoxane solution is removed when the solvent is stripped off Any trihydrocarbyl aluminum that is present in the solid recovered after the vacuum stripping, is not considered to have a significant effect upon the calculated aluminum value. Using this method, the atomic ratio of the boron in the boroxine to calculated Al in the aluminoxy units of the aluminoxane employed will be in the range of about 1/20 to about 1/3, more preferably about 1/15 to about 1/5, still more preferably about 1/7. As noted above, the commercial aluminoxane solutions generally contain at least some trihydrocarbyl aluminum, in addition to aluminoxy units. Generally, the trihydrocarbyl aluminum accounts for about about 0.1 to about 35 weight percent of the aluminum in the solution. It is generally preferred for the boroxine to be employed in such an amount that the molar ratio of the boroxine to the trihydrocarbyl aluminum be at least about 0.3334/1.

The mixed metallocene catalyst systems of this invention are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene- 1, 3-ethylbutene-1, heptene-1, octene-1, decene-1, 4,4-dimethyl-1-pentene, 4,4-diethyl-1-hexene, 3-4-dimethyl-1-hexene, and the like and mixtures thereof. The catalyst systems are particularly useful for preparing copolymers of ethylene or propylene and generally a minor amount, i.e. about 20 mole percent or less, more commonly about 15 mole percent or less, still more typically less than about 10 mole percent, of the higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

A further understanding of the present invention and its objects and advantages will be provided by a review of the following specific examples.

Various characteristics of the polymer and the polymerization were characterized. Examples of characteristics determiend in various cases include density in grams/mL (ASTM D1505-68); High Load Melt Index in grams of polymer/10 minutes 190° C. (ASTM D1238, Condition E); Melt Index in grams of polymer/10 minutes 190° C. (ASTM D1238, Condition E); molecular weights by size exclusion chromatography, i.e. weight averge molecular weight referred to herein as $M_w$, and number average molecular weight referred to herein as $M_n$; heterogenity index determined by dividing $M_w$ by $M_n$. The (SEC) size exclusion chromatography was conducted using a linear column capable of resolving the wide range of molecular weights generally observed in polyolefins, such as polyethylene.

EXAMPLE I

Preparation and Evaluation of Supported Unbridged Metallocene

Bis(n-butylcyclopentadienyl)zirconium dichloride supported on precipitated solid organoaluminoxane was employed in the polymerizations below.

Methylaluminoxane (MAO) obtained from Schering as a 10 weight percent MAO solution in toluene was precipitated by slurrying 7.2 pounds of the MAO solution with 6 gallons of hexane at room temperature. After stirring for one hour, 300 mL of a toluene solution containing 32 grams of $[(MeO)BO]_3$ was added dropwise to the slurry over a one hour period with stirring. The thus produced organoaluminoxy solids were then filtered and dried. The process was repeated three times and the produced solids were combined.

Bis(n-butylcyclopentadienyl)zirconium dichloride, was prepared by reacting 3 g (24.6 mmol) n-butylcyclopentadiene dissolved in diethylether and 15.4 mL (24.6) n-butyllithium dissolved in hexane at 0° C. with stirring for 3 hours. Then 2.86 g (12.3 mmol) $ZrCl_4$ was added in portions over a 20 minute period with vigorous stirring. The resulting slurry was stirred at room temperature for 2 hours and then the ether was removed under vacuum. The residue was extracted with two 100 mL hexane portions and then filtered. The resulting brown solution was cooled to 10° C. After standing overnight the colorless precipitated metallocene was collected and dried under vacuum.

Then 60 g (1.03 moles) of the boroxine precipitated MAO and a 100 mL hexane solution containing 0.835 g (0.00207 moles) bis(n-BuCp)$ZrCl_2$ were slurried in 500 mL hexane for three hours at room temperature. The thus produced solid organoaluminoxy supported metallocene was filtered and dried. Another batch produced using the same reactants and ratios in a similar manner was combined with the solids and the combined solids were employed as the catalyst system in the polymerizations below.

The resulting unbridged metallocene/solid organoaluminoxy catalyst system was then evaluated for the homopolymerization of ethylene. The polymerization was conducted in a 1-gallon stirred autoclave reactor. Approximately 0.043 1 gm of the metallocene/solid aluminoxy catalyst system was combined with 2 liters of isobutane in the reactor under a counterflow of ethylene at ambient temperature. The reactor was also charged with a known amount of hydrogen determined by a 20 psi pressure drop from a 300 cc pressure vessel. The reactor was brought to a polymerization temperature of about 80° C. and maintained at that temperature for about 30 minutes. The total reactor pressure was about 450 psig. Then the reactor was vented and isobutane was removed and the polymer was collected as a dry fluff. This polymerization provided a productivity of 6,719 gm of polymer per gram of metallocene/solid aluminoxy catalyst system/hour. The polymer had a melt index of 2.5 and a shear response, i.e. HLMI/MI, of 36.5. The molecular weight distribution was evaluated using size exclusion chromatography. This indicated that the weight average molecular weight was 79,630, the number average molecular weight was 10,220, and the heterogenity index was 7.8. The molecular weight distribution showed only one main peak. The heterogenity index was consistent with the relatively narrow molecular weight distribution often seen for unbridged metallocenes.

A similar polymerization was carried out using the unbridged metallocene/solid aluminoxy catalyst system. In this case, the amount of catalyst system employed was 0.0379 gm. The hydrogen addition was lower, i.e., a 6.4 psig pressure drop from the 300 cc pressure vessel. The temperature reaction was 90° C. In this case, the polymerization was carried out for about one hour. Otherwise the polymerization conditions were as described in the preceding paragraph. After the polymerization had been carried out for one hour, the isobutane diluent was removed and the solid polymer recovered and evaluated. The productivity of this polymerization was 3,720 gm of polymer per gram of unbridged metallocene/solid aluminoxy catalyst system/per hour. The melt index of the polymer was 2.46 and the shear response was 24.4. The weight average molecular weight was 83,210 and the heterogenity index was 4.3. Again, this molecular weight distribution showed only a single peak and was somewhat narrower than that of the preceding polymerization.

EXAMPLE II

Preparation and Evaluation of Bridged Catalyst Solution

The bridged metallocene 1,2-bis(9-fluorenyl) ethane zirconium dichloride was prepared using a procedure of the type generally disclosed in published European Patent Application No. 524,624. A solution of this bridged metallocene was then prepared by combining 43 mg of the bridged fluorenyl-containing metallocene with 49 mL of a 10 wt. percent methylaluminoxane toluene solution obtained from Ethyl Corporation to result in a bridged metallocene/methylaluminoxane catalyst solution.

The resulting bridged metallocene/methylaluminoxy catalyst solution was then evaluated for the homopolymerization of ethylene. The conditions employed were analogous to those set forth in Example I. Specifically, 2 liters of isobutane was used as the diluent. 10 psi of hydrogen was employed as determined by a pressure drop from a 300 cc vessel. The polymerization was conducted using 2 mL of the catalyst solution and a total pressure of 450 psig. The polymerization was begun at about 90° C. and was terminated after about one hour. The total polymer recovered was 102 gm. The polymer had a melt index of zero and a high load melt index of 1.1. This illustrates that the bridged metallocene produced a much higher molecular weight material than the unbridged metallocene employed in Example I.

EXAMPLE III

Bridged/Unbridged Catalyst System

In this experiment, a polymerization was conducted using a mixture of the catalyst system of Example I and the catalyst system of Example II. The polymerization involved the homopolymerization of ethylene. The addition of hydrogen in this case was 25 psig from a 300 cc vessel. The polymerization temperature was about 90° C. The amount of the unbridged catalyst system of Example I employed was 0.0392 gm. About 2 mL of the catalyst system of Example II was diluted with 18 mL of toluene and then 2 mL of this diluted catalyst system was combined with the unbridged catalyst system. The resulting polymer was recovered and evaluated as previously described for the other examples. The polymer had a melt index of 4.46. The shear response was 46.4. The molecular weight distribution illustrated a clear multi-modal distribution, i.e. these were two distinct peaks. The weight average molecular weight was 264,000 and the heterogenity index was 21. This molecular weight distribution clearly illustrates that both the bridged and unbridged metallocenes contributed to the polymer product. It further shows that the bridged metallocene certainly introduced a higher molecular weight component to the end product polymer.

EXAMPLE IV

Copolymerization with Unbridged Metallocene

A series of copolymerizations were carried out using the unbridged metallocene (9-methylfluorenyl)(cyclopentadienyl) zirconium dichloride. This metallocene can be prepared as disclosed in the aforementioned copending patent application Ser. No. 08/226,600. The unbridged metallocene was employed in conjunction with a solid organoaluminoxy product produced by reacting methoxyboroxine with a toluene solution of methylaluminoxane.

The solid organoaluminoxy cocatalyst was prepared by charging 6 gallons of hexane to a 10 gallon stirred reaction vessel. Then 7.3 pounds of an Ethyl Corporation 10 weight percent toluene solution of MAO was charged. The mixture was then stirred for about 1 hour. A toluene solution of methoxyboroxine was prepared by combining 48.7 gm of methoxyboroxine with 300 mL of toluene. This solution was slowly charged to the stirred reaction vessel over a 1 hour period. The mixture was then stirred for about 6 hours. Then the stirrer was stopped and the liquid was decanted. The resulting solid was then mixed with 2 gallons of hexane and washed. The solids were collected on a filter and dried in vacuo.

Then four polymerization reactions were conducted which involved the copolymerization of ethylene with hexene in a stirred 1 gallon autoclave at 90° C. for about 1 hour. In each case, a known quantity of the solid boroxine precipitated methylaluminoxane was charged to the autoclave followed by the addition of 1 mg of the unbridged metallocene in toluene. Then 2 liters of isobutane was charged. A known amount of hydrogen corresponding to a 115 psi pressure drop from a 30 cc vessel was added. Then the polymerization vessel was pressurized with 450 psig of ethylene and 30 gm of 1-hexene was added. The results are summarized in Table I.

TABLE I

| Run | g Solid MAO | Yield (g) | Activity g PE g Cat. Hr | MI | HLMI | SR | Density g/mL | $M_w/1000$ | $M_n/1000$ | HI |
|---|---|---|---|---|---|---|---|---|---|---|
| 1 | 0.1488 | 77.17 | 519 | 8280 | — | — | 0.9689 | 11.3 | 2.42 | 4.7 |
| 2 | 0.1724 | 90.09 | 523 | 2070 | — | — | 0.9640 | 13.6 | 2.64 | 5.2 |
| 3 | 0.1603 | 72.93 | 455 | 8280 | — | — | 0.9646 | 11.0 | 2.15 | 5.1 |
| 4 | 0.1597 | 86.70 | 543 | 20.5 | 636.9 | 31 | 0.9599 | 49.3 | 5.57 | 8.9 |

The column referring to activity refers to the grams of polyethylene produced per gram of total catalyst system per hour including both the metallocene and the solid boroxine precipitated methylaluminoxane.

The results demonstrate that the unbridged metallocene produced polymer having a relatively narrow molecular weight distribution, i.e. an HI in the range of 4.7 to 8.9. The molecular weight distributions consisted of only one main discernable narrow peak. The high density of the polymer obtained indicates that the unbridged metallocene was not particularly effective at incorporating the comonomer.

EXAMPLE V

Bridged Supported Catalyst System

The metallocene employed in this catalyst preparation was bis(9-fluorenyl)(dimethyl)silyl zirconium dichloride. The catalyst preparation involved charging 800 mL hexane containing 30 grams of fumed silica having the tradename Cab-O-Sil L-90 to the reactor vessel, flushing the reactor vessel with nitrogen and then charging the reactor vessel with 6 gallons of hexane. Then 7.2 lb of a 10 weight percent methylaluminoxane toluene solution obtained from Ethyl Corporation was charged to the reactor. The mixture was allowed to stir for 1 hour. A toluene solution of methoxyboroxine was prepared by dissolving 47.5 gm of the boroxine in 300 mL of toluene. This trimethoxyboroxine solution was then charged to the reactor vessel. The resulting slurry was stirred for 3 hours. The resulting solids were transferred to 5 gallon carboxy and the liquid was decanted. The solids were then washed several times with 3 gallon quantities of hexane. The solids were added to the clean reactor. Then 0.5 gallons of hexane were added. A slurry of the bridged metallocene was prepared by combining freely ground bis-(fluorenyl) (dimethyl)silyl zirconium dichloride with 300 mL of hexanes. This resulting slurry was then charged to the reaction vessel. The mixture was stirred for 4 hours and allowed to stand for 76 hours. The reactor vessel was cooled to 10° C. and then ethylene was charged to the reactor to raise the pressure of the reactor to about 40 psi and the resulting mixture was stirred for about 1 hour. The resulting prepolymerized solid catalyst was then recovered, filtered and subjected to drying using a vacuum. The resulting solid is considered to be about 25 wt. % ethylene prepolymer.

EXAMPLE VI

Evaluation of Bridged Supported Catalyst Systems

A series of polymerizations were carried out using the solid prepolymerized bridged catalyst system prepared in Example V. In some of the polymerizations, the solid bridged catalyst system was used in the absence of any unbridged metallocene and in other runs, a combination of the unbridged metallocene of Example IV was also used. The polymerizations were carried out in the same manner as described in Example IV. The variables involved and a summary of the results are provided in Table II.

TABLE II

| Run | Bridged grams | Unbridged grams | Hexene grams | Total psig | Yield, g | Activity | MI | HLMI | SR | Density | $M_w/1000$ | $M_n/1000$ | HI |
|---|---|---|---|---|---|---|---|---|---|---|---|---|---|
| 5 | 0.1500 | 0.0000 | 30 | 450 | 55.06 | 367 | 0.00 | 0.85 | — | 0.0249 | 180 | 7.83 | 23.0 |
| 6 | 0.1530 | 0.0000 | 30 | 450 | 37.37 | 244 | 0.00 | 1.59 | — | 0.9218 | 163 | 6.73 | 24.2 |
| 7 | 0.1560 | 0.0000 | 30 | 450 | 42.15 | 270 | 0.01 | 2.22 | 281 | 0.9230 | 234 | 7.95 | 29.4 |
| 8 | 0.1440 | 0.0010 | 30 | 450 | 41.31 | 287 | 0.19 | 104.81 | 559 | 0.9318 | 186 | 2.94 | 63.3 |
| 9 | 0.1380 | 0.0010 | 30 | 450 | 44.29 | 321 | 0.46 | 276.00 | 601 | 0.9412 | — | — | — |
| 10 | 0.1460 | 0.0020 | 30 | 450 | 36.15 | 248 | 6.66 | 690.00 | 104 | 0.9463 | 121 | 2.4 | 50.4 |
| 11 | 0.1400 | 0.0010 | 30 | 450 | 64.74 | 462 | 0.45 | 460.00 | 1018 | 0.9453 | 199 | 3.08 | 64.6 |
| 12 | 0.1220 | 0.0005 | 15 | 450 | 22.47 | 184 | 0.00 | 5.75 | — | 0.9372 | 198 | 3.15 | 62.9 |
| 13 | 0.1460 | 0.0010 | 15 | 450 | 32.12 | 220 | 0.20 | 111.89 | 563 | 0.9442 | 153 | 2.56 | 59.8 |
| 14 | 0.3974 | 0.0005 | 30 | 550 | 107.47 | 270 | 0.02 | 8.50 | 483 | 0.9401 | 290 | 3.95 | 73.4 |
| 15 | 0.4259 | 0.0010 | 30 | 550 | 69.67 | 164 | 0.03 | 10.16 | 308 | 0.9460 | 227 | 3.11 | 73.0 |
| 16 | 0.3933 | 0.0015 | 30 | 550 | 111.79 | 284 | 0.07 | 25.63 | 360 | 0.9478 | 248 | 3.75 | 66.1 |

Runs 5–6 illustrate that the solid prepolymerized bridged catalyst system produced a higher molecular weight product than that produced by the unbridged catalyst system of Example IV. Further, the results indicate that the solid bridged catalyst system was much more effective in incorporating the hexene than was the unbridged catalyst system as reflected by the densities of about 0.92. The molecular weight distributions were broader than that of the polymers produced using the unbridged catalyst system of Example IV, viz. HI's in the range of 23 to 29. The major peak in the molecular weight distribution was located in the high molecular weight end and there was evidence of two slightly smaller peaks at the low molecular weight end of the molecular weight distribution with the smallest peak being at the lowest molecular weight end of the distribution.

The activities reported in Table II are based upon the total weight of the catalyst system less the prepolymer on the solid unbridged portion of the catalyst system. The polymers made using the mixed catalyst system had a much broader molecular weight distribution than those produced using only the bridged catalyst system, i.e. HI's in the range of 50 to 73.

The polymers produced in Runs 8–13 exhibited a multimodal molecular weight distribution with two discernable peaks, with the larger peak being in the low molecular weight end. The densities of the polymers produced using the mixed catalyst were significantly lower than those using only the unbridged catalyst, which indicates that there was comonomer incorporation. In view of the low cocatalyst incorporation efficiency of the unbridged component, it follows that the majority of the monomer incorporation has occurred in the higher molecular weight portion of the polymer product.

Runs 14–16 were carried out using higher levels of hydrogen than the previous runs, specifically Runs 14 and 16 used approximately twice as much hydrogen and Run 15 used approximately three times as much hydrogen. In addition, in those runs more of the bridged solid metallocene was employed in the catalyst system. The polymers produced in solid aluminoxy product that is used as a cocatalyst for the unbridged metallocene control runs.

The solid organoaluminoxy cocatalyst was prepared by adding 6 gallons of hexane to a 10 gallon glass lined reactor and then adding 7.25 lbs. of 10 wt. percent toluene solution of methylaluminoxane obtained from Ethyl Corporation. This mixture was stirred for 1 hour and then 300 mL of a toluene solution containing 32 grams of methoxyboroxine was added over a 1 hour period with stirring. The resulting slurry was then stirred for 6 hours. The solids were allowed to settle overnight. About 5 gallons of the liquid was decanted. Then the solids were washed with 1 gallon of hexane for 1 hour with stirring. And then the majority of the liquid was decanted.

The various catalysts were evaluated for their effectiveness in the copolymerization of ethylene and hexene. The polymerization conditions were analogous to those described in Example IV.

A summary of the variables involved and results obtained is provided in Table III.

TABLE III

| Run No. | Bridged, mg | Unbridged, mL | Solid MAO | $H_2$, psig | Hexane, g | MI | HLMI | Density | $M_w/1000$ | HI |
| --- | --- | --- | --- | --- | --- | --- | --- | --- | --- | --- |
| 17 | — | 1.7 | 54.6 | 15 | 15 | 26.43 | 685.0 | 0.9566 | 55.69 | 3.083 |
| 18 | — | 5.0 | 14.4 | 50 | 45 | 1.1878 | 22.64 | 0.9379 | 100.63 | 4.684 |
| 19 | 165.4 | — | — | 50 | 45 | 0 | .0619 | 0.9155 | 465.07 | 10.008 |
| 20 | 103.9 | 2 | — | 50 | 45 | 2.94 | 119.13 | 0.9492 | 135.49 | 10.21 |
| 21 | 92.1 | 2 | — | 100 | 15 | 2.47 | 122.69 | 0.9582 | 91.36 | 13.77 |
| 22 | 86.7 | 3.2 | — | 100 | 15 | 2.27 | 115.77 | 0.9559 | 102.5 | 18.68 |
| 23 | 158.7 | — | — | 50 | 45 | 0 | 0.6121 | 0.9213 | 288.78 | 8.970 |
| 24 | 153.4 | 5 | — | 50 | 30 | 0.3758 | 21.41 | 0.9452 | 167.17 | 8.305 |
| 25 | 151.4 | 5 | — | 50 | 15 | 0.3616 | 43.04 | 0.9554 | 92.53 | 8.265 |

Runs 14–16 each have somewhat broader molecular weight distribution than the polymers produced in Runs 8–13. In addition, the molecular weight was distributed in a bimodal fashion with the most intense peak in the high molecular weight end. The polymers produced from Runs 14–16 were evaluated for environmental stress crack resistance [Condition B (10% Igepal)]. All three polymers had a ESCR value in excess of 1000 hours. This clearly demonstrates that the inventive polymers have particularly good environmental stress crack resistance. This data further indicates that the mixed metallocene catalyst system is capable of producing resins suitable for blow molding, pipe, and high molecular weight film applications.

EXAMPLE VII

A series of polymerizations were conducted to compare the effects of a mixed catalyst system prepared from the unbridged metallocene bis(n-butylcyclopentadienyl) zirconium dichloride and the bridged metallocenes bis(fluorenyl)(dimethyl)silyl zirconium dichloride and bis(fluorenyl)(diphenyl)silyl zirconium dichloride.

The unbridged metallocene was employed as a hexane solution containing 0.2 mg of bis(n-butylcyclopentadienyl) zirconium dichloride per milliliter. In the control runs using only the unbridged metallocene, the metallocene was employed in combination with a solid organoaluminoxy product produced by precipitating methylaluminoxane with methoxyboroxine.

The bridged catalysts were employed in the form of a product produced by supporting the metallocene on the same Runs 17 and 18 were copolymerizations carried out using the unbridged metallocene without any bridged metallocene present. Run 19 was carried out using the cocatalyst supported bridged metallocene bis(fluorenyl) (diphenyl)silyl zirconium dichloride. Runs 20–22 involved the use of both the supported bridged metallocene and the unbridged metallocene. Run 23 employed only the cocatalyst supported bridged metallocene bis(fluorenyl) (dimethyl)silyl zirconium dichloride. Runs 24 and 25 employed the combination of the supported bis(fluorenyl)(dimethyl)silyl zirconium dichloride and the unbridged metallocene.

A comparison of control run 18 and control run 23 reveals that the unbridged metallocene was not as effective in incorporating the comonomer as was the bridged metallocene as reflected by the difference in the density of the polymers obtained. Similarly the bis(fluorenyl) diphenyl zirconium dichloride was more effective in incorporating comonomer than was the unbridged metallocene.

A comparison of control run 19 with control run 23 reveals that the (diphenyl)silyl zirconium dichloride metallocene produced a higher molecular weight polymer than the (dimethyl)silyl bridged metallocene. A comparison of runs 18 and 20 shows that the mixed catalyst produced a polymer having a somewhat higher density than the polymer produced using only the unbridged catalyst. It is also noted that the inventive runs 20–22 produced a polymer having a much broader molecular weight distribution than that of the polymer produced using only the unbridged metallocene. The molecular weight and density results indicate that both the unbridged and bridged metallocenes contributed to the production of polymer.

The molecular weight distribution of the polymer produced in control run 19 exhibited a major peak at the high molecular weight end and a minor peak in the low molecular weight end of the molecular weight distribution. The minor peak was less than one-fourth the height of the major peak. The molecular weight distribution of the polymer produced in inventive run 20 exhibited one peak which demonstrated an obvious increase in the amount of low molecular weight polymer over that present in the polymer obtained in control run 19. The polymer produced in inventive run 21 had a molecular weight distribution exhibiting two peaks, the major peak being at the high molecular weight end and the minor peak being at the low molecular weight end, with the minor peak being almost half as high as the high molecular weight peak. The polymer produced in inventive run 22 exhibited a molecular weight distribution similar to that of the polymer obtained in inventive run 21. However, in this case the separation of the two peaks was more discernable a greater separation in the molecular weights of the produced polymers.

The polymers produced in runs 23–25 had molecular weight distributions appearing as mainly one peak; however, the polymers produced in inventive runs 24 and 25 demonstrated the contribution of the unbridged metallocene in the low molecular weight end of the molecular weight distribution was more noticeable than for the polymer produced by control run 23.

This data demonstrates that the mixed catalyst of the present invention can be employed to produce polymers having a wide range of properties depending upon the particular ratios of the catalyst used, the amounts of comonomer used, and the amounts of hydrogen used.

That which is claimed is:

1. A catalyst system suitable for preparing a polyolefin having a molecular weight distribution, $M_w/M_n$, greater than 3 from an olefin or or mixture of olefins comprising
   (1) at least first and second different metallocenes characterized by the fact that said first metallocene is a bridged metallocene which contains a fluorenyl group and said second metallocene is an unbridged metallocene and by the fact that said first metallocene if used as the sole metallocene to prepare polyolefin, would produce a higher molecular weight than said second metallocene would produce if used as the sole metallocene under the same polymerization conditions, and
   (2) a suitable cocatalyst for the metallocenes.

2. A catalyst system according to claim 1 wherein said first metallocene is more effective in incorporating comonomer than said second metallocene under the same polymerization conditions.

3. A catalyst system according to claim 2 wherein said first metallocene is one for which hydrogen produces a smaller change in polymer molecular weight that for said second metallocene under the same polymerization conditions.

4. A catalyst system according to claim 1 wherein said catalyst system is prepared by supporting said first metallocene on a solid form of alkyl aluminoxane that is substantially insoluble in the polymerization medium under the polymerization conditions and then combining that supported metallocene with said second metallocene.

5. A catalyst system according to claim 4 wherein said solid form of alkyl aluminoxane is prepared by contacting a solution of an organoaluminoxane with an organo boroxine under conditions sufficient to produce a solid suitable for use as a cocatalyst for a metallocene.

6. A catalyst system according to claim 5 wherein said first metallocene is a fluorenyl-containing bridged metallocene of the formula (Z)—R'—(Z') Me Qk wherein R' is an organo group linking Z and Z'; Z is a substituted or unsubstituted fluorenyl radical; Z' is a substituted or unsubstituted fluorenyl radical, a substituted or unsubstituted indenyl radical, a substituted or unsubstituted cyclopentadienyl radical, an octahydrofluorenyl, or a tetrahydroindenyl radical, said substituents on Z and Z' being selected from hydrocarbyl or hydrocarbyloxy radicals containing 1 to 10 carbon atoms; Me is a transition metal selected from Ti, Zr, and Hf; each Q is selected from the group consisting of hydrogen, alkyl groups containing 1 to 10 carbon atoms, alkoxy groups containing 1 to 10 carbon atoms, aryl groups containing 6 to 10 carbon atoms, aryloxy groups containing 6 to 10 carbon atoms, alkenyl groups containing 2 to 10 carbon atoms, arylalkyl groups containing 7 to 40 carbon atoms, alkylaryl groups containing 8 to 40 carbon atoms, and halogens; k is a number sufficient to fill the valences of Me.

7. A catalyst system according to claim 1 wherein the metallocenes of said catalyst system consist essentially of said first and second metallocenes and said metallocenes are zirconium-containing metallocenes.

8. A catalyst system according to claim 7 wherein said first metallocene is selected from the group consisting of 1,2-bis-(fluorenyl) ethane zirconium dichloride, bis-(fluorenyl)(dimethyl) silyl zirconium dichloride, bis(fluorenyl)(diphenyl) silyl zirconium dichloride, (fluorenyl)-methylene(cyclopentadienyl) zirconium dichloride, and (indenyl)-ethylene-(fluorenyl) zirconium dichloride and said second metallocene is selected form the group consisting of (cyclopentadienyl)(fluorenyl) zirconium dichloride, bis-(n-butyl cyclopentadienyl) zirconium dichloride, (indenyl)(pentamethylcyclopentadienyl) zirconium dichloride, (9-methylfluorenyl)(cyclopentadienyl) zirconium dichloride, and bis-(9-methylfluorenyl) zirconium dichloride.

* * * * *

UNITED STATES PATENT AND TRADEMARK OFFICE
CERTIFICATE OF CORRECTION

PATENT NO. : 5,534,473

DATED : July 9, 1996

INVENTOR(S) : M. Bruce Welch et al

It is certified that error appears in the above-identified patent and that said Letters Patent is hereby corrected as shown below:

Column 17, line 36, after "olefin", please delete the first occurrence of "or".

Column 18, line 1, after "weight", please delete "that" and insert therefor ---than---.

Column 18, line 45, please delete "form" and insert therefor ---from---.

Signed and Sealed this

Thirty-first Day of December, 1996

Attest:

BRUCE LEHMAN

*Attesting Officer*      *Commissioner of Patents and Trademarks*